(12) United States Patent
Goble et al.

(10) Patent No.: US 9,700,426 B2
(45) Date of Patent: *Jul. 11, 2017

(54) MULTIPLE FACET JOINT REPLACEMENT

(71) Applicant: GLOBUS MEDICAL, INC., Audubon, PA (US)

(72) Inventors: E Marlowe Goble, Logan, UT (US); T Wade Fallin, Hyde Park, UT (US)

(73) Assignee: GLOBUS MEDICAL, INC., Audubon, PA (US)

( * ) Notice: Subject to any disclaimer, the term of this patent is extended or adjusted under 35 U.S.C. 154(b) by 109 days.

This patent is subject to a terminal disclaimer.

(21) Appl. No.: 14/178,722

(22) Filed: Feb. 12, 2014

(65) Prior Publication Data

US 2015/0223944 A1     Aug. 13, 2015
US 2016/0242924 A9     Aug. 25, 2016

Related U.S. Application Data

(63) Continuation of application No. 13/275,636, filed on Oct. 18, 2011, now Pat. No. 8,685,061, which is a continuation of application No. 12/616,216, filed on Nov. 11, 2009, now Pat. No. 8,066,772, which is a continuation of application No. 11/456,509, filed on Jul. 10, 2006, now Pat. No. 7,618,455, which is a continuation of application No. 10/420,467, filed on Apr. 22, 2003, now Pat. No. 7,074,237, which is a continuation of application No. 09/736,103, filed on Dec. 13, 2000, now Pat. No. 6,565,605.

(51) Int. Cl.
*A61F 2/44*     (2006.01)

(52) U.S. Cl.
CPC ......... *A61F 2/4405* (2013.01); *Y10S 606/907* (2013.01); *Y10S 606/91* (2013.01)

(58) Field of Classification Search
CPC .... A61F 2/4405; A61F 2/442; A61F 2/30767; A61F 2310/00634; A61F 2310/00017; A61F 2310/00023; A61F 2310/00029; A61F 2310/00604; A61F 2002/30168; A61F 2002/30177; A61F 2002/30578; A61F 2002/30708; A61F 2002/30878; A61F 2002/449; A61F 2230/0043; A61F 2230/0056; A61F 2250/0084; A61B 17/86
USPC ....... 606/246, 247, 248, 250, 257, 266, 279, 606/907, 909, 910; 623/17.11–17.16
See application file for complete search history.

(56) References Cited

U.S. PATENT DOCUMENTS 5,571,191 A * 11/1996 Fitz .............................. 623/17.11
6,132,464 A * 10/2000 Martin .................. A61F 2/4405
                                                   606/248

(Continued)

*Primary Examiner* — Pedro Philogene

(57) ABSTRACT

A prosthesis for the replacement of multiple diseased or traumatized spinal facets comprises a portion that replaces at least a bony portion of the facets to be replaced and where the prosthesis attaches to the vertebra in a manner that does not require attachment to, or abutment against, the lamina. Multiple configurations of the prosthesis provide for replacement of the two inferior facets, the two superior facets, a superior and inferior facet, or all four facets. A method of installing the prosthesis is provided that is comprised of the steps of resecting at least a portion of the facets that carry the diseased or traumatized spinal facets and attaching the prosthesis in a manner that does not require attachment or abutment against the lamina.

18 Claims, 17 Drawing Sheets

(56) References Cited

U.S. PATENT DOCUMENTS

| | | | | |
|---|---|---|---|---|
| 6,565,605 B2* | 5/2003 | Goble | ................... | A61F 2/4405 |
| | | | | 606/248 |
| 6,610,091 B1* | 8/2003 | Reiley | ................ | A61B 17/1671 |
| | | | | 606/246 |
| 6,811,567 B2* | 11/2004 | Reiley | ........................ | 623/17.11 |
| 7,377,942 B2* | 5/2008 | Berry | ........................ | 623/17.11 |

* cited by examiner

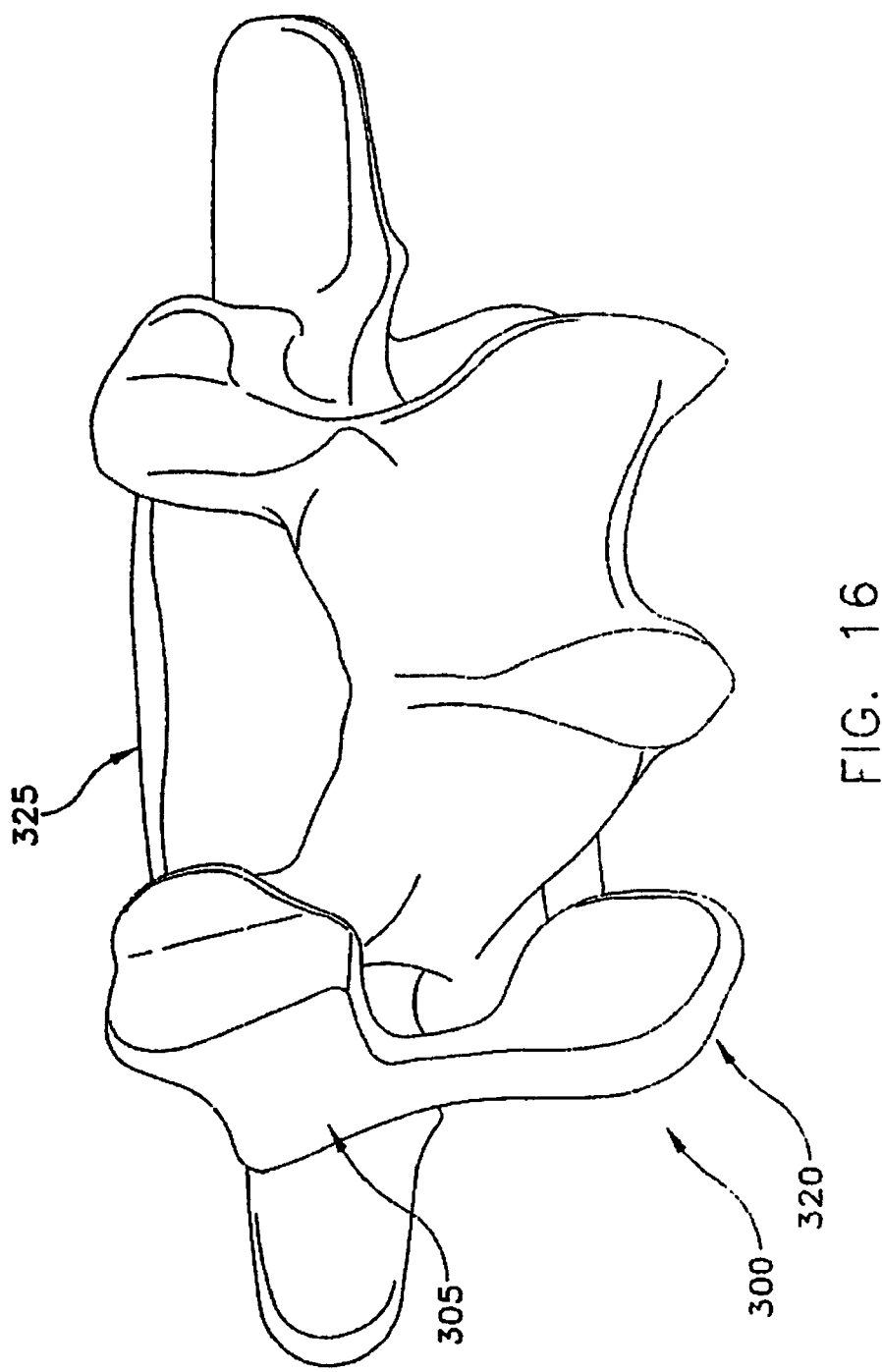

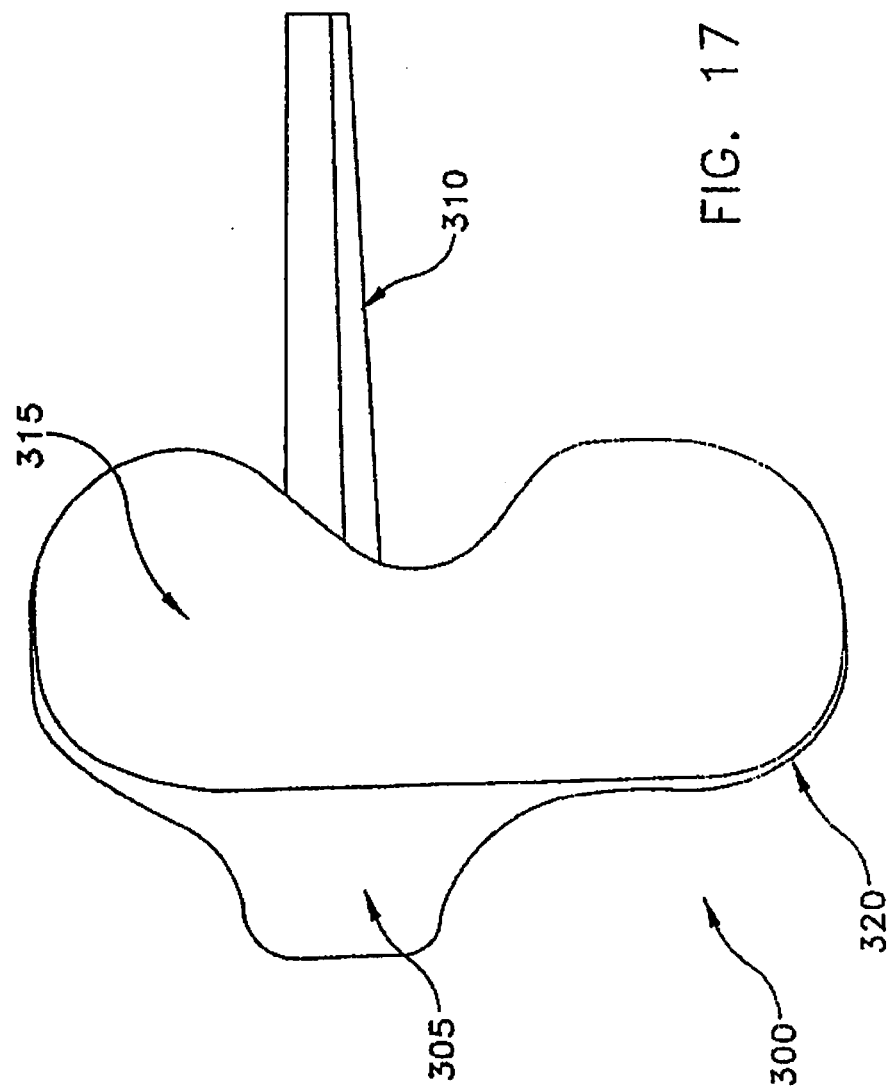

MULTIPLE FACET JOINT REPLACEMENT

CROSS-REFERENCE TO RELATED APPLICATIONS

This application is a continuation of U.S. application Ser. No. 13/275,636, filed on Oct. 18, 2011, which is a continuation of U.S. application Ser. No. 12/616,216, filed on Nov. 11, 2009, which issued as U.S. Pat. No. 8,066,772 on Nov. 29, 2011, which is a continuation of U.S. application Ser. No. 11/456,509, filed Jul. 10, 2006 and entitled MULTIPLE FACET JOINT REPLACEMENT, which issued as U.S. Pat. No. 7,618,455 on Nov. 17, 2009, which is a continuation of: U.S. application Ser. No. 10/420,467, filed Apr. 22, 2003 and entitled MULTIPLE FACET JOINT REPLACEMENT, which issued as U.S. Pat. No. 7,074,237 on Jul. 11, 2006, which is a continuation of U.S. application Ser. No. 09/736,103, filed Dec. 13, 2000 and entitled MULTIPLE FACET JOINT REPLACEMENT, which issued as U.S. Pat. No. 6,565,605 on May 20, 2003. Each of the disclosures listed above are incorporated herein by reference in their entirety.

BACKGROUND OF THE INVENTION

1. The Field of the Invention

The present invention relates to surgical devices and methods to replace a damaged, diseased, or otherwise painful spinal facet joint.

2. Description of Related Art

Traumatic, inflammatory, metabolic, synovial, neoplastic and degenerative disorders of the spine can produce debilitating pain that can have severe socioeconomic and psychological effects. One of the most common surgical interventions today is arthrodesis, or spine fusion, of one or more motion segments, with approximately 300,000 procedures performed annually in the United States. Clinical success varies considerably, depending upon technique and indications, and consideration must be given to the concomitant risks and complications. For example, it has been shown that spine fusion decreases function by limiting the range of motion for patients in flexion, extension, rotation, and lateral bending. Furthermore, it has been shown that spine fusion creates increased stresses and, therefore, accelerated degeneration of adjacent non-fused motion segments. Additionally, pseudoarthrosis, as a result of an incomplete or ineffective fusion, may reduce or even eliminate pain relief for the patient. Also, the fusion device, whether artificial or biological, may migrate out of the fusion site.

Recently, several attempts have been made to recreate the natural biomechanics of the spine by use of an artificial disc. Artificial discs provide for articulation between vertebral bodies to recreate the full range of motion allowed by the elastic properties of the natural intervertebral disc which directly connects two opposed vertebral bodies.

However, the artificial discs proposed to date do not fully address the mechanics of motion of the spinal column. In addition to the intervertebral disc, posterior elements called the facet joints help to support axial, torsional and shear loads that act on the spinal column. Furthermore, the facet joints are diarthroidal joints that provide both sliding articulation and load transmission features. The effects of their absence as a result of facetectomy has been observed to produce significant decreases in the stiffness of the spinal column in all planes of motion: flexion and extension, lateral bending, and rotation. Furthermore, contraindications for artificial discs include arthritic facet joints, absent facet joints, severe facet joint tropism or otherwise deformed facet joints.

U.S. Pat. No. Re. 36,758 to Fitz discloses an artificial facet joint where the inferior facet, the mating superior facet, or both, are covered with a cap. The cap requires no preparation of the bone or articular surfaces; it covers and, therefore, preserves the bony and articular structure.

The capping of the facet has several potential disadvantages. If the facet joint is osteoarthritic, a cap will not remove the source of the pain. Additionally, at least in the case of surface replacements for osteoarthritis femoral heads, the capping of articular bone ends has proven to lead to clinical failure by means of mechanical loosening. The clinical failure is hypothesized to be a sequela of disrupting the periosteum and ligamentum teres femoris, both serving a nutrition delivery role to the. femoral head, thereby leading to avascular necrosis of the bony support structure for the surface replacement. Another potential disadvantage is that in order to accommodate the wide variability in anatomical morphology of the facets, not only between individuals but also between levels within the spinal column, a very wide variety of sizes and shapes would be required.

U.S. Pat. No. 6,132,464 to Martin discloses a spinal facet joint prosthesis that is supported on the lamina, which is sometimes also referred to as the posterior arch of the vertebra. Extending from this prosthetic support structure are inferior and/or superior blades that replace the cartilage at the facet joint Like the Fitz design, the Martin prosthesis generally preserves existing bony structures and therefore does not address pathologies which affect the bone of the facets in addition to affecting the associated cartilage. Furthermore, the Martin invention requires a mating condition between the prosthesis and the lamina, or the posterior arch, that is a thin base of curved bone that carries all four facets and the spinous process. Since the posterior arch is a very complex and highly variable anatomic surface, it is very difficult to design a prosthesis that provides reproducible positioning to correctly locate the cartilage-replacing blades for the facet joints.

Another approach to surgical intervention for spinal facets is provided in WO9848717A1 to Villaret. While Villaret teaches the replacement of spinal facets, the replacement is interlocked in a manner to immobilize the joint.

Facet joint replacement in conjunction with artificial disc replacements represent a novel solution to recreating a fully functional motion segment that is compromised due to disease or trauma. Together, facet joint and disc replacement can eliminate substantially all sources of pain, return full function and range of motion, and restore the natural biomechanics of the spinal column. Additionally, degenerative or traumatized facet joints may be replaced in the absence of disc replacement when the natural intervertebral disc is unaffected by the disease or trauma.

It would therefore be an improvement in the art to provide a device and a method for the replacement of multiple vertebral facets and a portion of their associated bony structure so as to remove the source of traumatic, arthritic, or other disease related pain.

SUMMARY OF THE INVENTION

It is an object of the invention to provide a multiple vertebral facet replacement prosthesis for a diseased or traumatized vertebra with painful or compromised facet joints.

It is another object of the invention to provide a method of replacing multiple vertebral facets for a diseased or traumatized vertebra with painful or compromised facet joints.

It is yet another object of the present invention to provide a kit of multiple facet prostheses for the convenient replacement of one or more levels of facet joints.

In one preferred embodiment, the inferior bilateral facets of a superior vertebra are resected at the base of the facets where they connect to the posterior arch. Flanges are oriented relative to the body of the prosthesis such that when the flanges are placed against the pedicles and in a manner such that the planar surfaces of the flanges are perpendicular to the respective axes of the pedicle's interior bone canal, the articulating surfaces of the inferior bilateral facet prosthesis will be properly positioned to replicate the articulating surfaces of the natural facets. Each flange includes a hole for the passage of a fastener to securely attach the prosthesis to the pedicle. The fastener can be a screw, spike, tack, staple, modular post, or the like.

Alternatively, or in addition, the superior facets of an inferior vertebra are resected at the base of the facets where they connect to the pedicles. As with the bilateral inferior facet prosthesis, a bilateral superior facet prosthesis is attached to the inferior vertebra by means-of fasteners which engage holes on mounting flanges and the pedicles.

The fasteners or the bone contacting surfaces of the flanges may be porous coated to promote bone ingrowth in order to achieve long term fixation. The porous coating may carry osteoconductive agents, such as hydroxylapatite, calcium sulfate, or demineralized bone matrix. Alternatively, the porous coating may carry osteoinductive agents, such as bone morphogenic proteins, including rhBMP-2 and rhBMP-7.

Alternative embodiments of the present invention include the replacement of different combinations of facets on a single vertebra. One embodiment provides for the replacement of the left inferior and left superior facets by a single prosthesis. Another embodiment provides for the concurrent replacement of all four facets by a single prosthesis. The four facet prosthesis can be used in conjunction with a superior bilateral facet replacement and an inferior bilateral facet replacement to provide a two level replacement of facet joints. Alternatively, two of the four facet prostheses can be used in conjunction with a superior bilateral facet replacement and an inferior bilateral facet replacement to provide a three level replacement of facet joints, where the middle level facet replacement is accomplished by the two adjacent four facet prostheses.

The present invention has numerous advantages over the prior art. Among other things, the present invention provides for the convenient, simultaneous replacement of multiple combinations of facets on a single vertebra: two superior facets, two posterior facets, two left facets, two right facets, or all four facets. Furthermore, multiple levels of facet joints can be replaced by selecting from a kit of multiple facet joint prostheses. Another advantage of the present invention is a precise and tight attachment of the prosthesis to bones, as opposed to prosthetic surfaces that rely on mating with highly complex and variable external surfaces of the vertebra, such as the posterior arch. Another advantage is that the optional porous coating is placed into interior bone spaces where porous coatings have proven to achieve bone ingrowth for excellent long term fixation strength. This ability to achieve bone ingrowth is uncertain for the prior art devices that engage the external bone surfaces of the vertebra. Yet another advantage lies in the removal of the facet bone structure. More particularly, where the facet bone is involved in the disease pathology or the trauma that compromised the articular or cartilaginous surface of the facet, resection provides a means for ensuring that all pain associated with the disease or trauma is removed. With prior art devices, the bony structure of the facets is generally left intact.

The above, and other, objects, features and advantages of the present invention will become apparent from the following description which is to be read in conjunction with the accompanying drawings.

BRIEF DESCRIPTION OF THE DRAWINGS

FIG. 16 is a perspective view of an implanted superior and inferior unilateral facet prosthesis; and FIG. 17 is a perspective view of the unilateral facet prosthesis shown in FIG. 16.

DETAILED DESCRIPTION OF THE PREFERRED EMBODIMENTS

Figure 1:
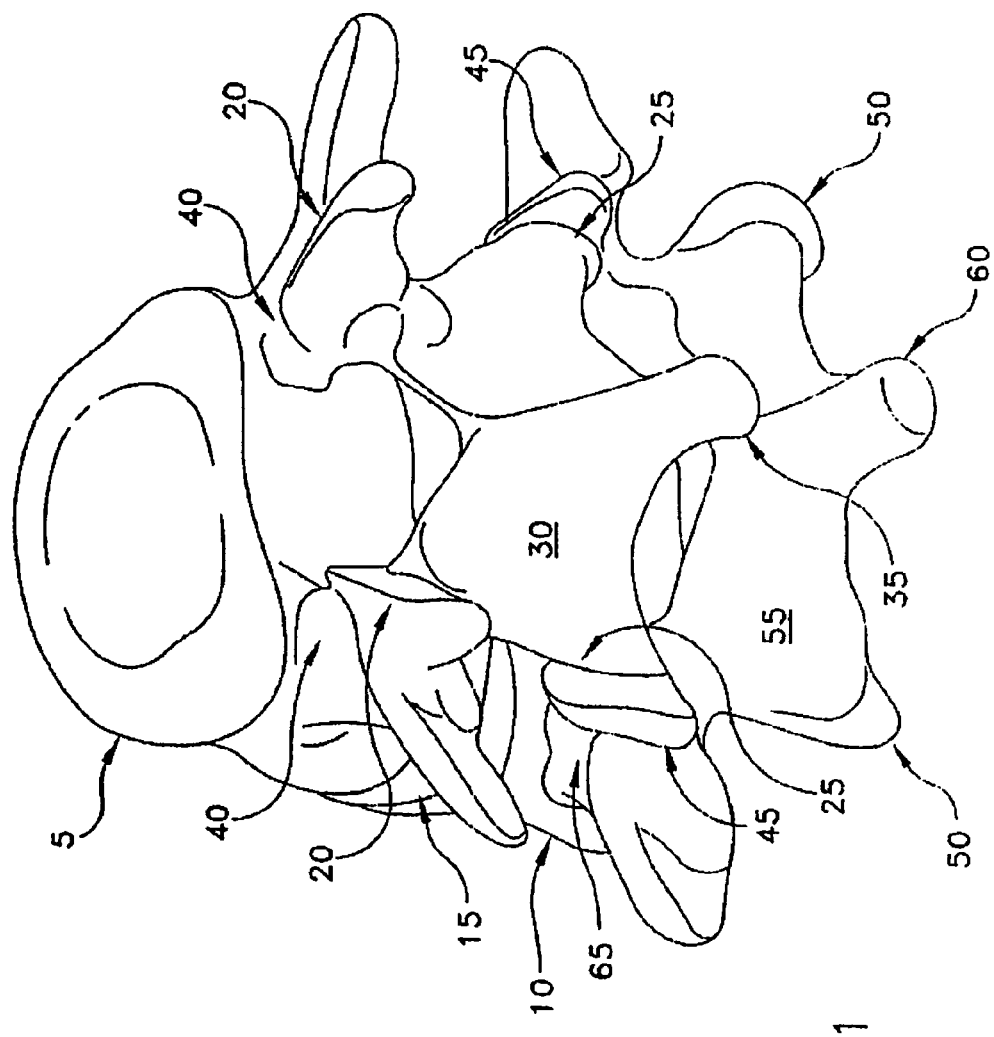
FIG. 1 is a perspective view of a spine motion segment.

Referring first to FIG. 1, there is shown a superior vertebra 5 and an inferior vertebra 10, with an intervertebral disc 15 located in between. Vertebra 5 has superior facets 20, inferior facets 25, a lamina (also sometimes referred to as a posterior arch) 30, a spinous process 35, and pedicles 40. Vertebra 10 has superior facets 45, inferior facets 50, a posterior arch 55, a spinous process 60, and pedicles 65 (only one of which is seen in FIG. 1).

Figure 2:
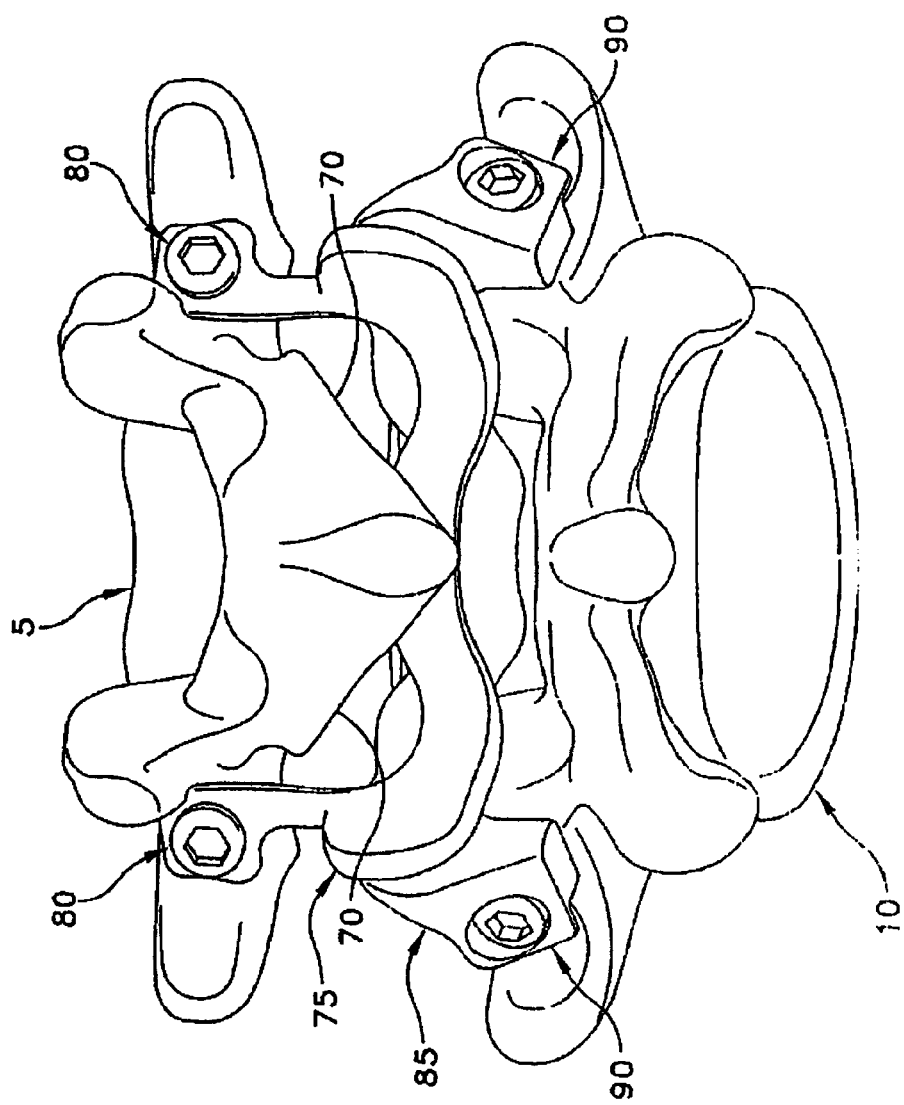
FIG. 2 is a dorsal view of a bilateral facet joint reconstructed in accordance with the present invention.

Referring now to FIG. 2, the left and right inferior facets 25 of vertebra 5 have been resected at 70 and a bilateral inferior facet prosthesis 75 has been attached to vertebra 5 using screw fasteners 80. Similarly, the left and right superior facets 45 of vertebra 10 have been resected at 82 (FIG. 7) and a bilateral superior facet prosthesis 85 has been attached to vertebra 10 using screw fasteners 90.

Figure 3:
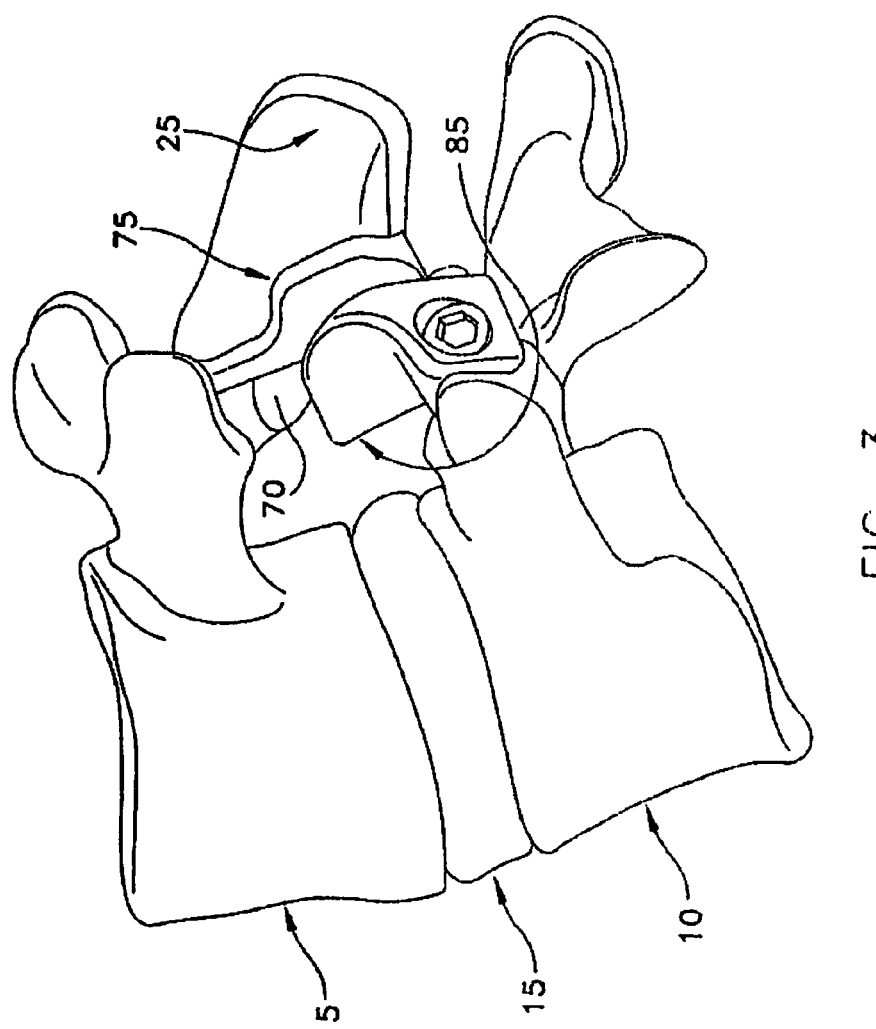
FIG. 3 is a lateral view of the bilateral facet joint prosthesis shown in FIG. 2.

In FIG. 3 it can be appreciated that bilateral inferior facet prosthesis 75 replicates the natural anatomy when compared to the intact inferior facet 25 of vertebra 5. Furthermore, bilateral facet prosthesis 75 extends from its attachment point in a manner that does not require contact with, or mating to, the complex geometry of the lamina (or posterior arch) 30. Resection surfaces 70 provide adequate clearance for bilateral inferior facet prosthesis 75 and provide complete removal of the diseased or traumatized natural inferior facets 25.

Figure 4:
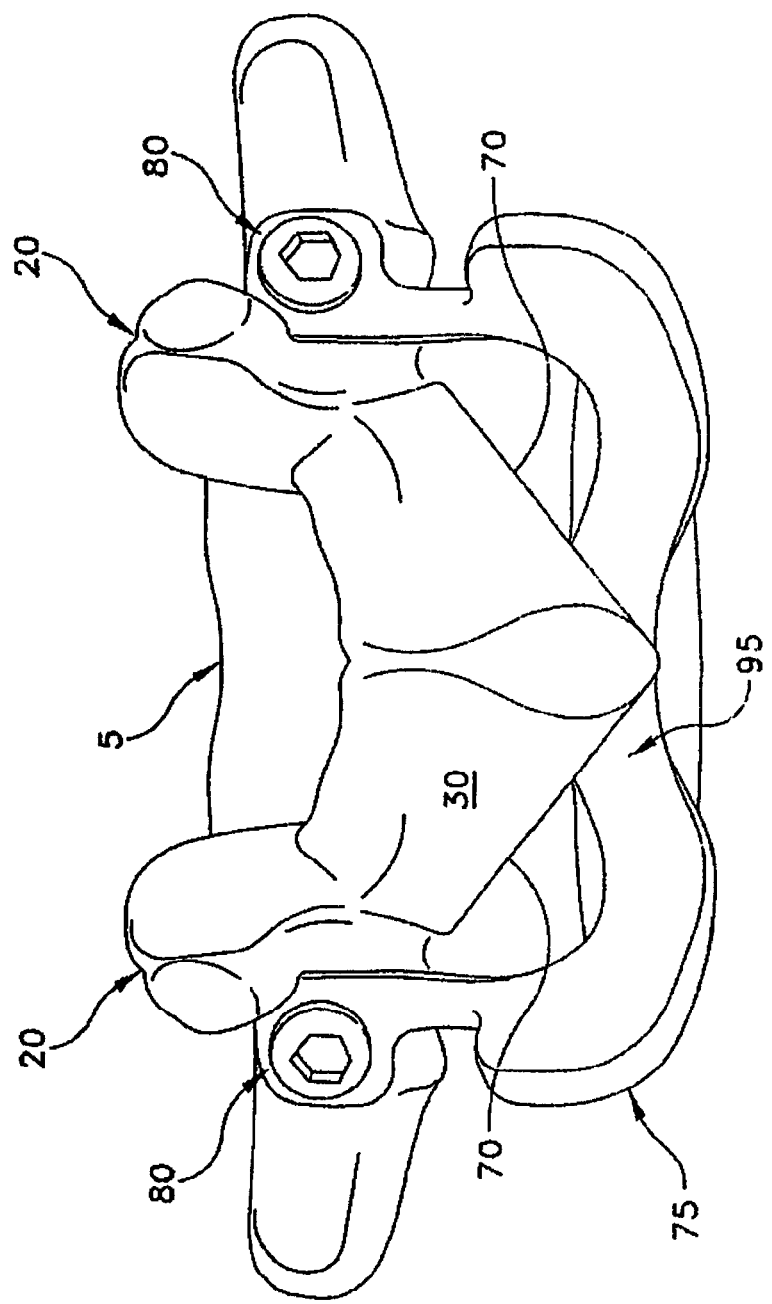
FIG. 4 is a dorsal view of the implanted inferior bilateral facet prosthesis shown in FIGS. 2 and 3.
Figure 5:
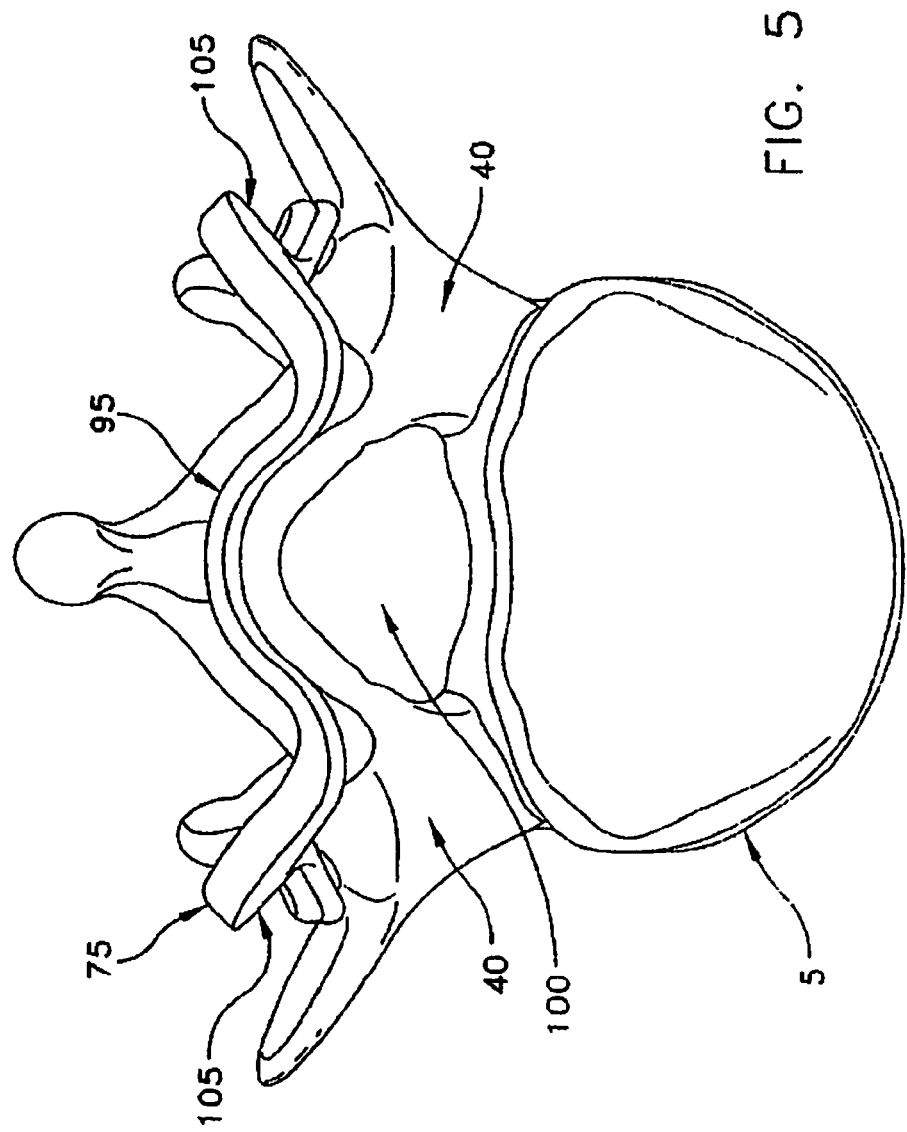
FIG. 5 is an inferior view of the implanted inferior bilateral facet prosthesis shown in FIGS. 2 and 3.

FIGS. 4 and 5 illustrate how the geometry of the bridge 95 of bilateral inferior facet prosthesis 75 matches that of the posterior arch 30 of vertebra 5 in order to provide adequate clearance for the central foramen 100. Articular surfaces 105 articulate with the opposing superior facets 45 (or their prosthetic replacements) of the vertebra 10.

Figure 6:
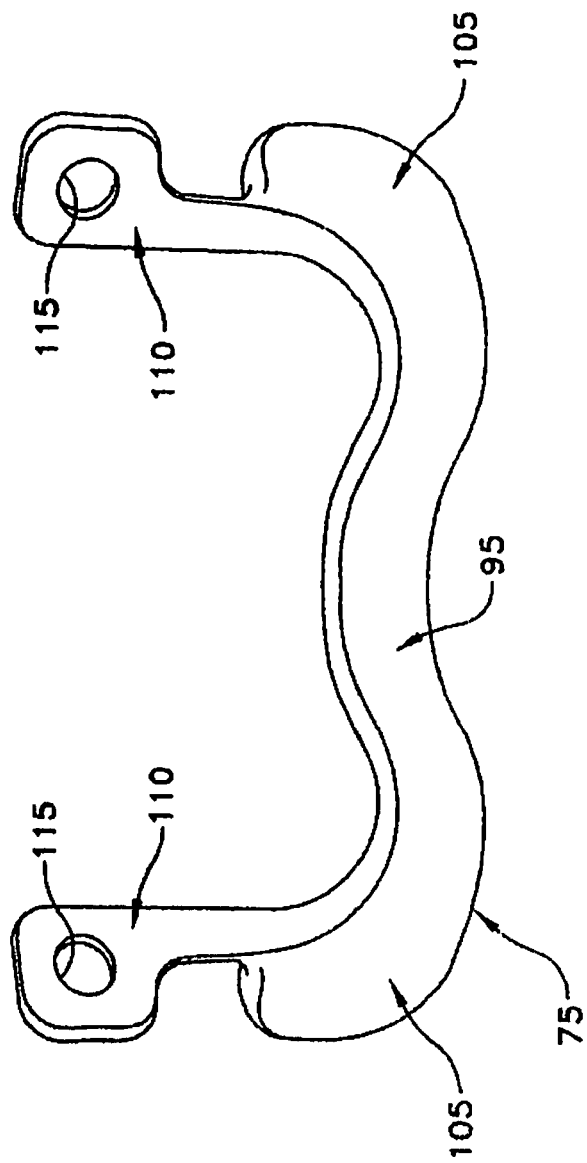
FIG. 6 is a ventral view of the inferior bilateral facet prosthesis shown in FIGS. 4 and 5.

FIG. 6 illustrates the bilateral inferior facet prosthesis 75 with flanges 110 that abut against the pedicles 40 of vertebra 5. Bridge 95 connects the articular surfaces 105. Holes 115 allow the attachment of bilateral inferior facet prosthesis 75 to vertebra 5 by means of screw fasteners 80. Alternatively, screw fasteners 80 could be replaced with staples, pins, tacks, anchors, modular fixation posts, or the like. These alternative fasteners could further include porous coatings to further enhance bony fixation, and could also include osteoconductive or osteoinductive substances.

Figure 7:
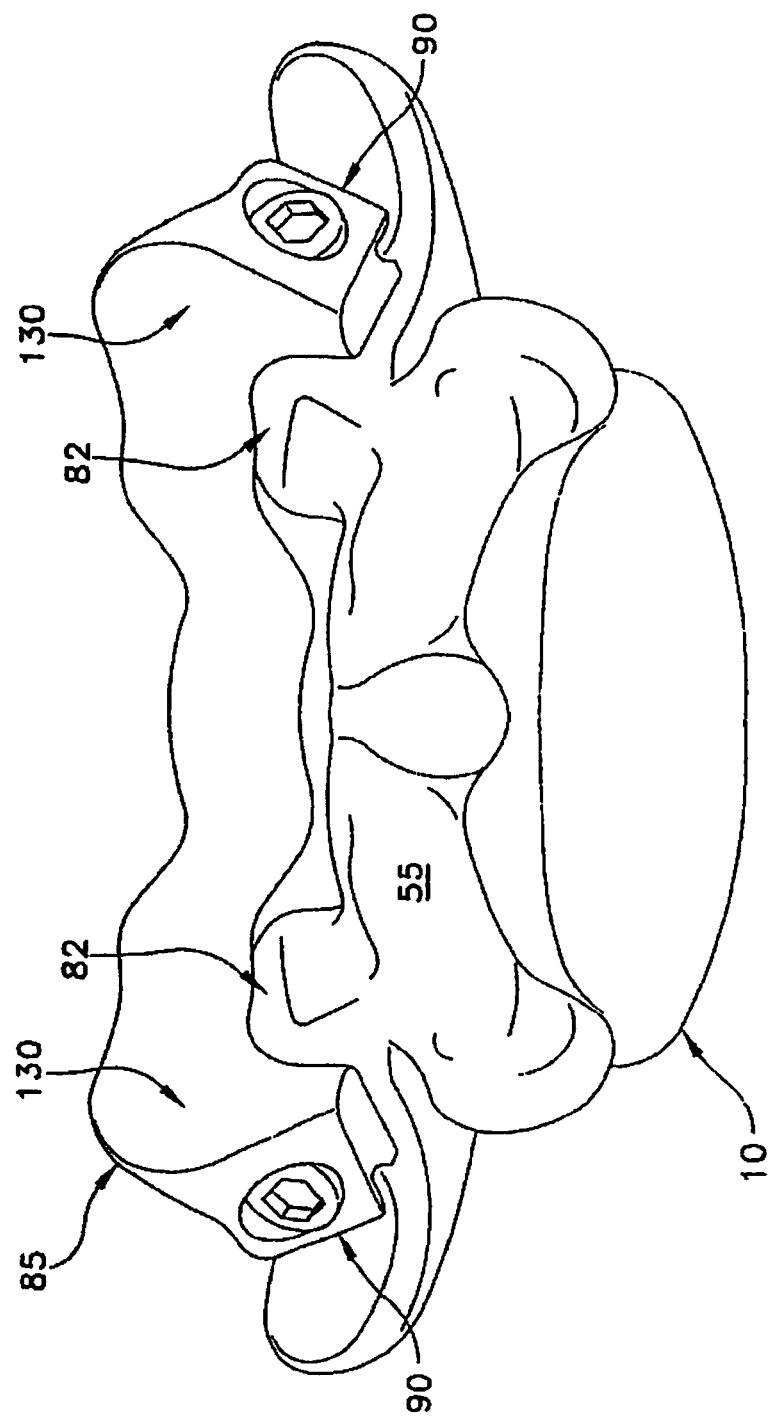
FIG. 7 is a dorsal view of the implanted superior bilateral facet prosthesis shown in FIGS. 2 and 3.

In FIG. 7 it can be appreciated that bilateral superior facet prosthesis 85 replicates the natural anatomy when compared to the intact superior facets 45 of vertebra 10. Furthermore, bilateral facet prosthesis 85 extends from its attachment point in a manner that does not require contact with, or mating to, the complex geometry of the lamina (or posterior arch) 55. Resection surfaces 82 provide adequate clearance for bilateral superior facet prosthesis 85 and provide complete removal of the diseased or traumatized natural superior facets 45.

Figure 8:
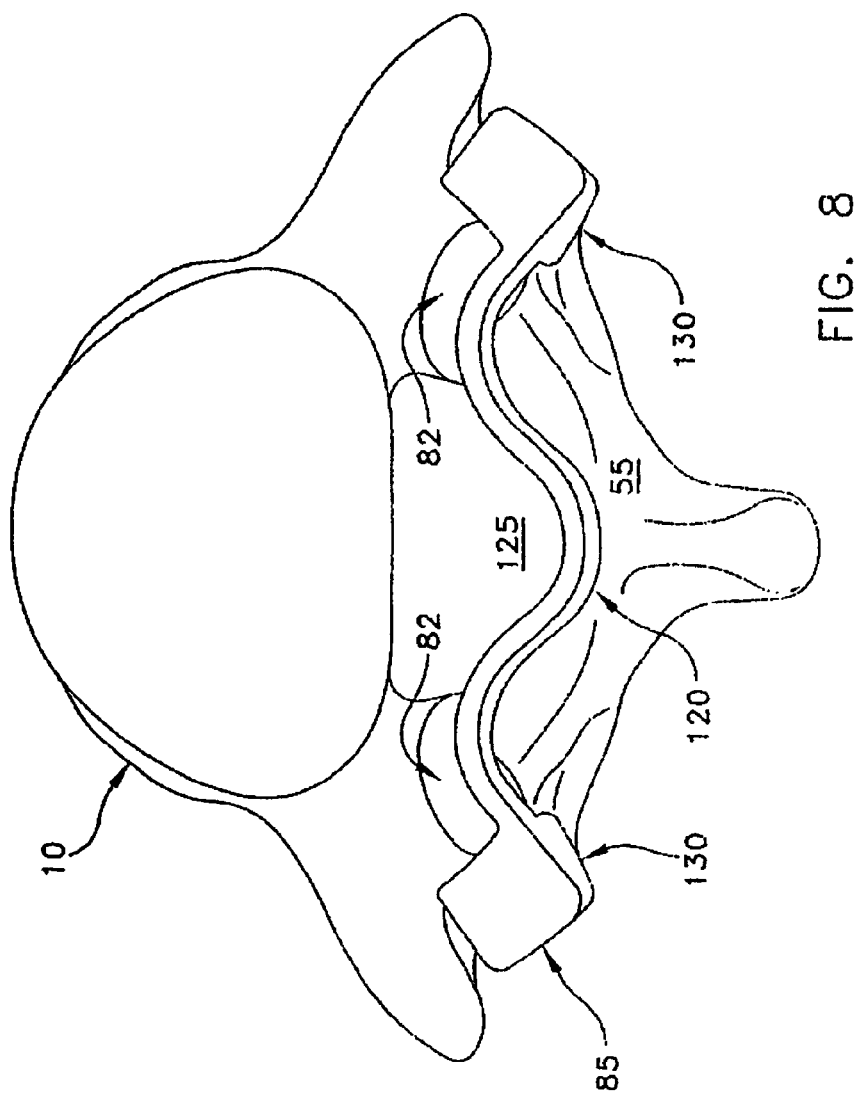
FIG. 8 is a superior view of the implanted superior bilateral facet prosthesis shown in FIGS. 2 and 3.

FIG. 8 illustrates how the geometry of the bridge 120 of bilateral superior facet prosthesis 85 matches that of the posterior arch 55 of vertebra 10 in order to provide adequate clearance for the central foramen 125. Articular surfaces 130 articulate with the opposing inferior facets of the vertebra 5.

Figure 9:
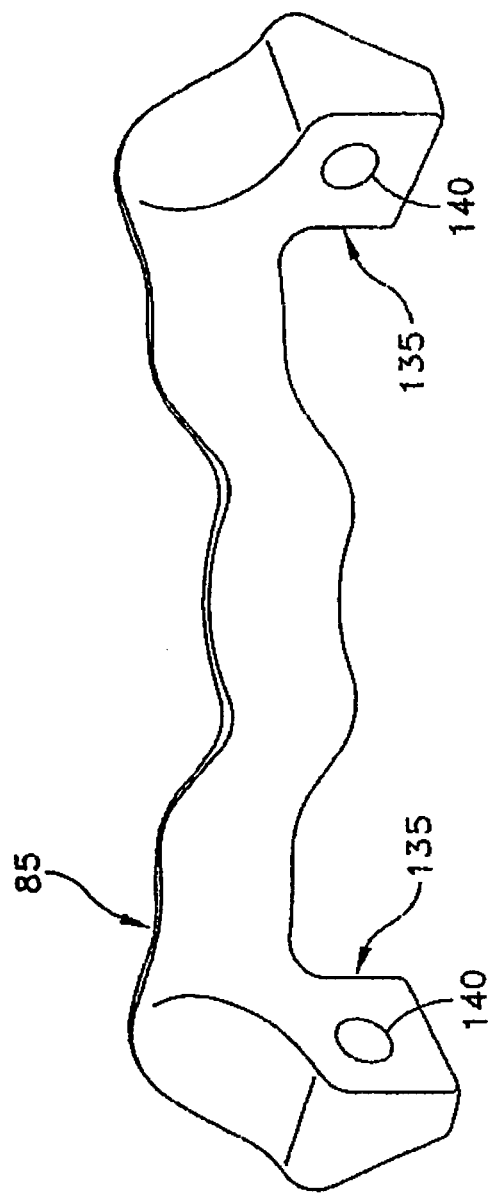
FIG. 9 is a ventral view of the superior bilateral facet prosthesis shown in FIGS. 7 and 8.

FIG. 9 illustrates the bilateral superior facet prosthesis 85 with flanges 135 that abut against the pedicles 65 of vertebra 10. Bridge 120 connects the articular surfaces 130 (seen in FIG. 8 but not seen in FIG. 9). Holes 140 allow the attachment of bilateral superior facet prosthesis 85 to vertebra 10 by means of screw fasteners 90.

Figure 10:
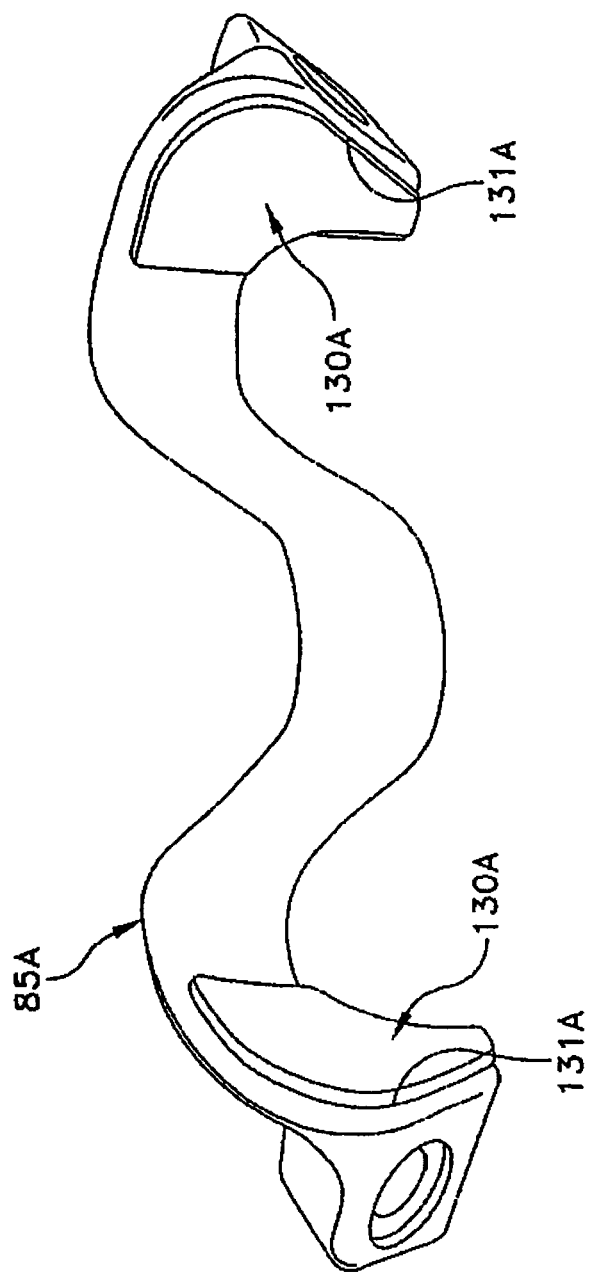
FIG. 10 is a perspective view of an alternative embodiment of the superior bilateral facet prosthesis shown in FIGS. 7 and 8.

FIG. 10 illustrates an alternative superior facet prosthesis 85A with a bearing surface 130A that mounts to substrate 131A. The bearing surface 130A is preferably a biocompatible polymeric material, such as ultra high molecular weight polyethylene. Alternately, the bearing surface 130A can be ceramic, such as zirconia or alumina. The substrate 131A is preferably a biocompatible metal alloy, such as an alloy of titanium, cobalt, or iron.

Figure 11:
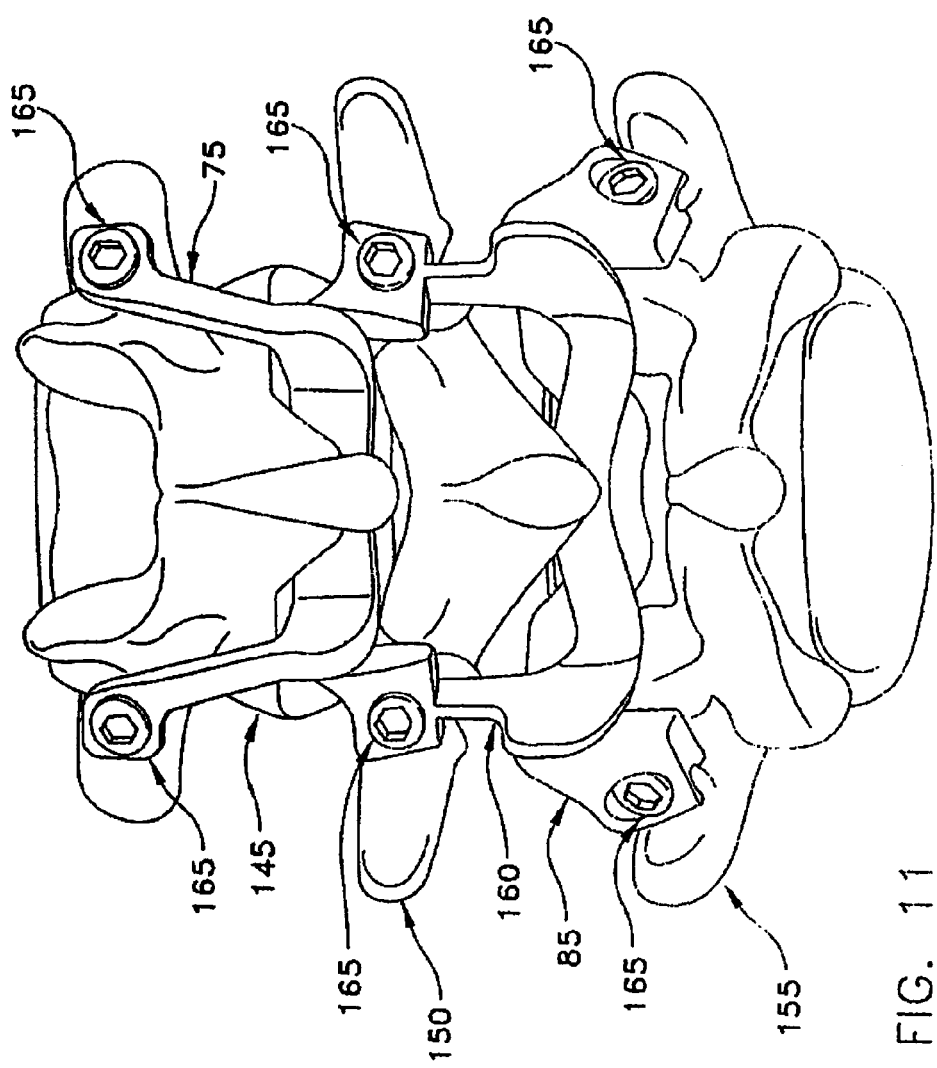
FIG. 11 is a dorsal view of a two level facet joint replacement.

FIG. 11 illustrates a superior vertebra 145, a middle vertebra 150, and an inferior vertebra 155. Superior facet prosthesis 85 articulates with quad-facet prosthesis 160 to recreate the natural biomechanics of the replaced facet joints. Inferior facet prosthesis 75 articulates with quad-facet prosthesis 160 to recreate the natural biomechanics of the replaced facet joints at the next upper level. Thus, FIG. 11 illustrates a two level reconstruction of facet joints. Superior facet prosthesis 85, quad-facet prosthesis 160, and inferior facet prosthesis 75 are each attached to bone by means of screw fasteners 165.

Figure 12:
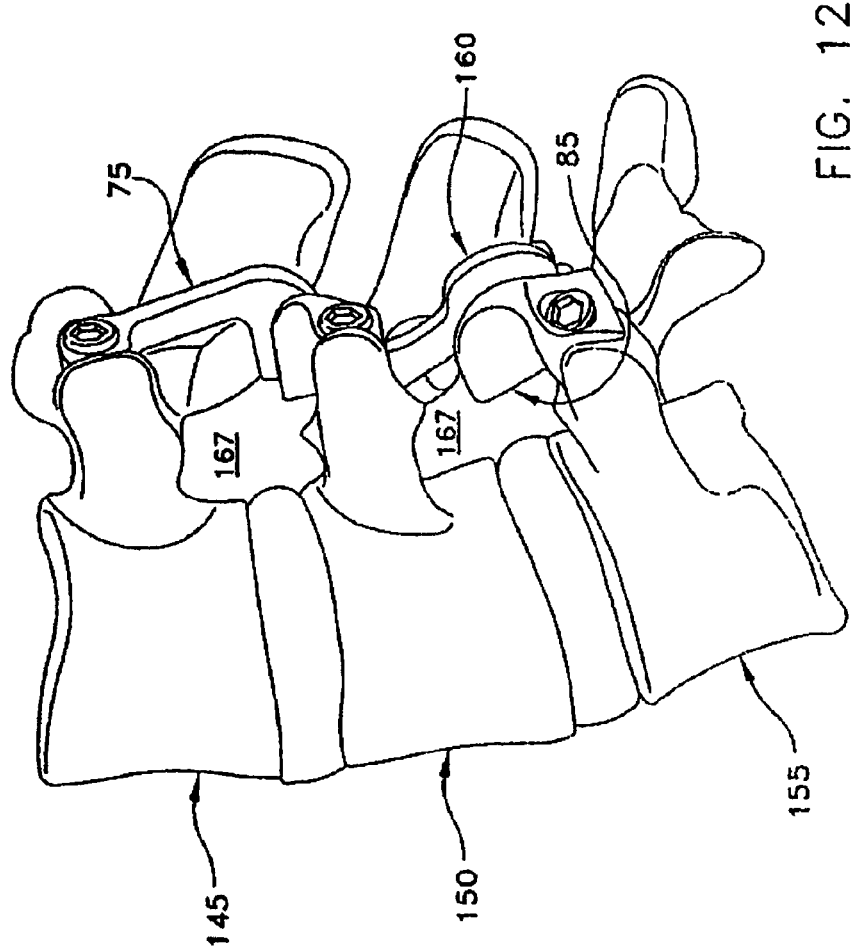
FIG. 12 is a lateral view of the two level facet joint replacement of FIG. 11.

In the lateral view of FIG. 12, it can be appreciated that superior facet prosthesis 85, quad-facet prosthesis 160, and inferior facet prosthesis 75 do not encroach into the intervertebral foraminal spaces 167 where nerve roots extend laterally from the spinal cord.

Figure 13:
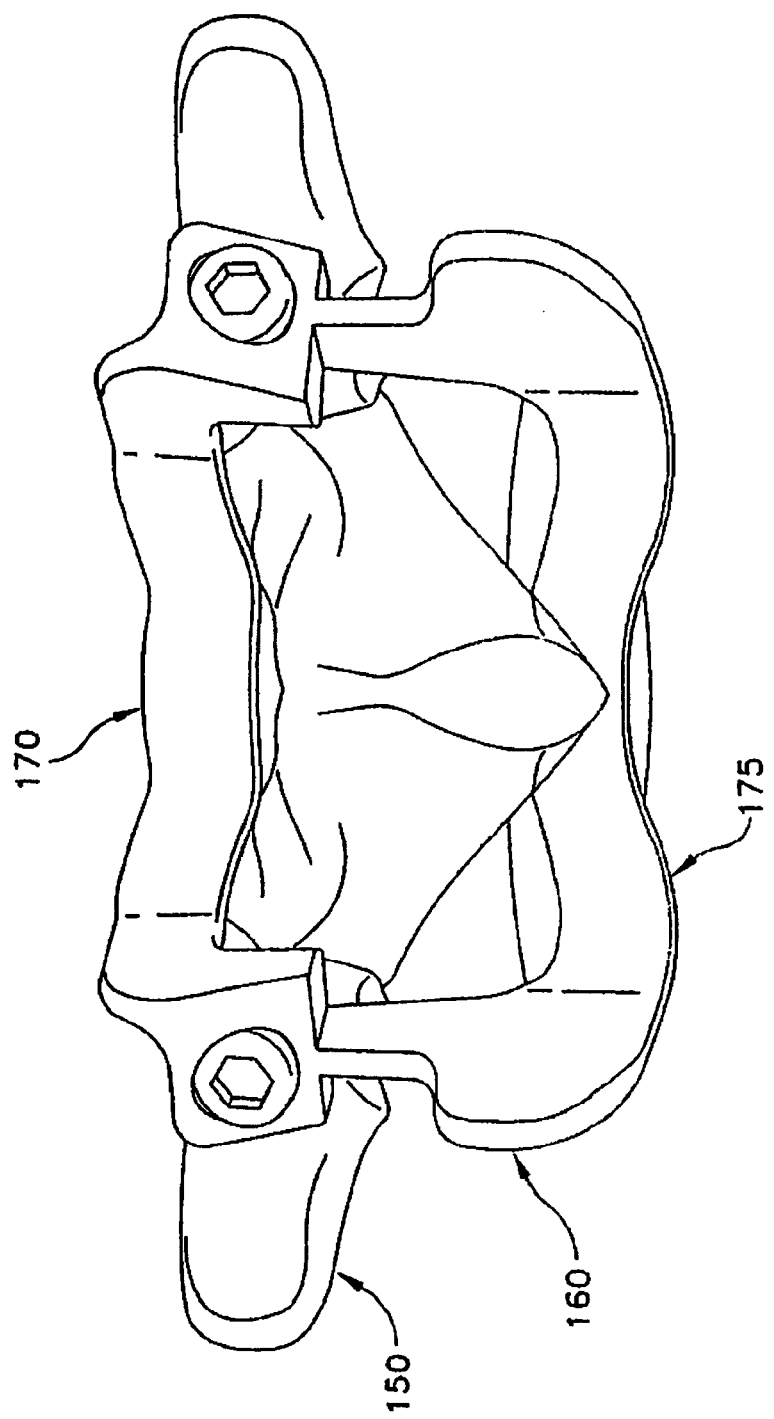
FIG. 13 is a dorsal view of the implanted four facet prosthesis shown in FIGS. 11 and 12.
Figure 14:
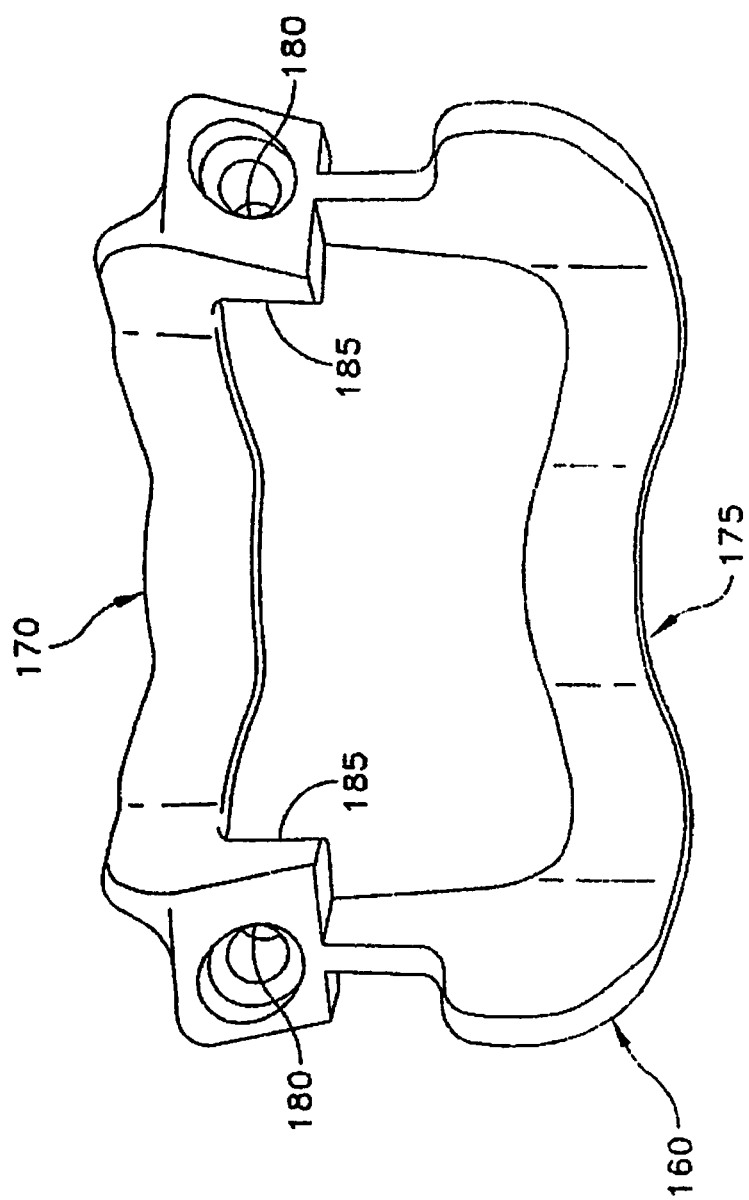
FIG. 14 is a perspective view of the four facet prosthesis shown in FIG. 13.

Referring next to FIG. 13, it should be appreciated that superior bridge 170 and inferior bridge 175 of quad-facet prosthesis 160 do not contact any portion of vertebra 150. Mounting holes 180 (shown in FIG. 14) are used to secure the flanges 185 against the pedicles of vertebra 150.

Figure 15:
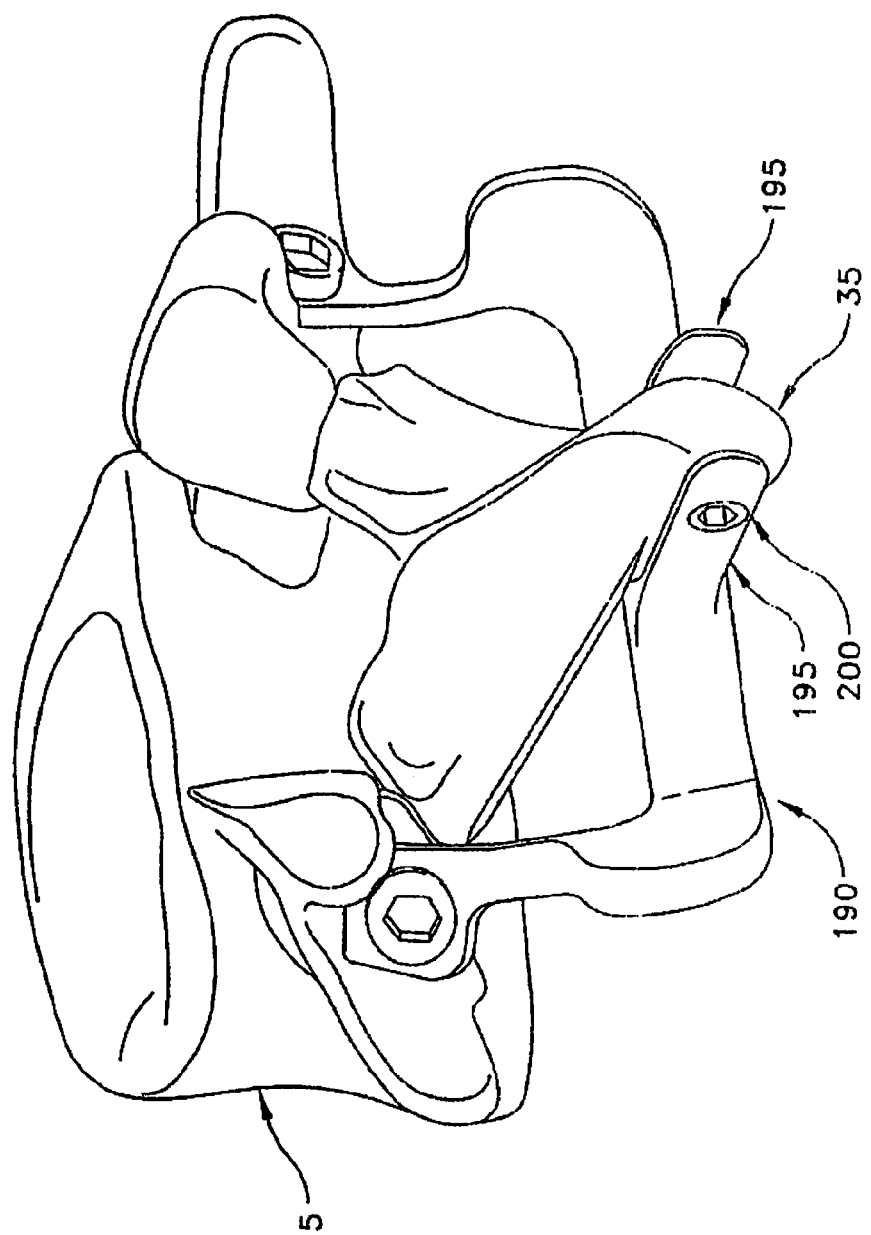
FIG. 15 is a perspective view of an alternative form of inferior bilateral facet prosthesis.

In FIG. 15, an alternative inferior bilateral facet prosthesis 190 is presented. To further stabilize the implant and to counter moments. that act upon the two points of fixation into the pedicles, a set of parallel flanges 195 extend posteriorly such that the two flanges straddle the spinous process 35. A bolt 200 is used to fasten the parallel flanges to the spinous process. Alternatively, other adjunctive structural features could be added to further stabilize the prosthesis. For example, a strut that extends, and attaches, to the transverse process could be used to further stabilize the prosthesis.

Looking next at FIGS. 16 and 17, there is shown a superior and inferior unilateral facet prosthesis 300. Unilateral facet prosthesis 300 comprises a body 305 and a stem 310 extending out of body 305. A superior element 315 extends vertically upward from body 305, and an inferior element 310 extends vertically downward from body 305. Unilateral facet prosthesis 300 is configured so that when its stem 310 extends into the pedicle of vertebra 325, superior element 315 will replace a resected superior facet, and inferior element 320 will replace a resected inferior facet. If desired, stem 310 could be replaced with a screw extending through a hole in body 305 and into the pedicle.

Having described preferred embodiments of the invention with reference to the accompanying drawings, it is to be understood that the embodiments shown herein are by way of example and not limitation, and that various changes and modifications may be effected by one skilled in the art without departing from the scope or spirit of the invention as defined in the following claims.

The invention claimed is:
1. A surgical method comprising:
resecting at least a portion of a left inferior facet;
resecting at least a portion of a right inferior facet;
inserting a left inferior facet prosthetic component into the resected left inferior facet via a fastener;
inserting a right inferior facet prosthetic component into the resected right inferior facet via a fastener, wherein the left inferior facet prosthetic component and the right inferior prosthetic component are connected via a bridge having first and second parallel flanges extending posteriorly from the bridge, wherein the bridge is configured to extend along a natural spinous process formed between the left inferior facet and the right inferior facet without removing or attaching to the natural spinous process, the bridge having a curvature that matches a corresponding lamina and does not contact the lamina, and wherein the first flange extends along a first side of the spinous process and the second flange extends along an opposite side of the spinous process;
resecting at least a portion of a left superior facet;
resecting at least a portion of a right superior facet;
inserting a left superior facet prosthetic component into the resected left superior facet via a fastener; and
inserting a right superior facet prosthetic component into the resected right superior facet via a fastener.

2. The surgical method of claim 1, wherein the bridge is curved.

3. The surgical method of claim 1, wherein the left inferior facet prosthetic component does not contact a lamina.

4. The surgical method of claim 1, wherein the right inferior facet prosthetic component does not contact a lamina.

5. The surgical method of claim 1, wherein the left inferior facet prosthetic component and the right inferior prosthetic component are part of a single body.

6. The surgical method of claim 1, wherein left superior facet prosthetic component and the right superior facet prosthetic component are part of a single body.

7. The surgical method of claim 6, wherein the single body comprises a pair of flanges.

8. The surgical method of claim 7, wherein each of the flanges abuts against a pedicle of a vertebra.

9. A surgical method comprising:
resecting at least a portion of a left inferior facet;
resecting at least a portion of a right inferior facet;
inserting a left inferior facet prosthetic component into the resected left inferior facet via a fastener; and
inserting a right inferior facet prosthetic component into the resected right inferior facet via a fastener, wherein the left inferior facet prosthetic component and the right inferior prosthetic component are connected via a bridge having first and second parallel flanges extending posteriorly from the bridge, wherein the bridge is configured to extend along a natural spinous process formed between the left inferior facet and the right inferior facet without removing or attaching to the natural spinous process, the bridge having a curvature that matches a corresponding lamina and does not contact the lamina, and wherein the first flange extends along a first side of the spinous process and the second flange extends along an opposite side of the spinous process.

10. The surgical method of claim 9, wherein the left inferior facet prosthetic component and the right inferior prosthetic component are part of a single body.

11. The surgical method of claim 9, wherein the bridge is curved.

12. The surgical method of claim 9, wherein neither the left inferior facet prosthetic component nor the right inferior facet prosthetic component contacts a lamina.

13. The surgical method of claim 9, wherein the bridge does not contact any portion of a vertebra.

14. A surgical method comprising:
resecting at least a portion of a left superior facet;
resecting at least a portion of a right superior facet;
inserting a left superior facet prosthetic component into the resected left superior facet via a fastener; and
inserting a right superior facet prosthetic component into the resected right superior facet via a fastener, wherein the left superior facet prosthetic component and the right superior prosthetic component are connected via a bridge having first and second parallel flanges extending posteriorly from the bridge, wherein the bridge is configured to extend along a natural spinous process formed between the left superior facet and the right superior facet without removing or attaching to the natural spinous process, the bridge having a curvature that matches a corresponding lamina and does not contact the lamina, and wherein the first flange extends along a first side of the spinous process and the second flange extends along an opposite side of the spinous process.

15. The surgical method of claim 14, wherein the left superior facet prosthetic component and the right superior prosthetic component are part of a single body.

16. The surgical method of claim 14, wherein the bridge is curved.

17. The surgical method of claim 14, wherein the left superior facet prosthetic component and the right superior facet prosthetic component are connected to a pedicle.

18. The surgical method of claim 14, wherein the bridge does not contact any portion of a vertebra.

* * * * *